(12) United States Patent
Srivastava (10) Patent No.: US 10,564,094 B2
(45) Date of Patent: Feb. 18, 2020

(54) DEVICE AND METHOD FOR BLOOD HEMOGLOBIN MEASUREMENT WITHOUT CARBOXYHEMOGLOBIN INTERFERENCE

(71) Applicant: Ambar Srivastava, Ghaziabad (IN)

(72) Inventor: Ambar Srivastava, Ghaziabad (IN)

(*) Notice: Subject to any disclaimer, the term of this patent is extended or adjusted under 35 U.S.C. 154(b) by 0 days.

(21) Appl. No.: 14/412,459

(22) PCT Filed: Jul. 2, 2013

(86) PCT No.: PCT/IN2013/000406
§ 371 (c)(1),
(2) Date: Jan. 2, 2015

(87) PCT Pub. No.: WO2014/006638
PCT Pub. Date: Jan. 9, 2014

(65) Prior Publication Data
US 2015/0192512 A1    Jul. 9, 2015

(30) Foreign Application Priority Data
Jul. 3, 2012    (IN) .......................... 2074/DEL/2012

(51) Int. Cl.
*G01N 21/31* (2006.01)
*G01N 21/84* (2006.01)
*G01N 33/72* (2006.01)
*G01N 33/52* (2006.01)

(52) U.S. Cl.
CPC ......... *G01N 21/31* (2013.01); *G01N 21/8483* (2013.01); *G01N 33/525* (2013.01); *G01N 33/721* (2013.01); *G01N 2201/061* (2013.01); *G01N 2201/068* (2013.01)

(58) Field of Classification Search
CPC ........................... G01N 21/31; G01N 21/8483
See application file for complete search history.

(56) References Cited

U.S. PATENT DOCUMENTS

| | | | |
|---|---|---|---|
| 4,820,490 A * | 4/1989 | Morris | G01N 21/255 356/409 |
| 5,728,352 A * | 3/1998 | Poto | G01N 21/8483 422/403 |
| 2004/0048386 A1* | 3/2004 | Wu | G01N 33/721 436/66 |
| 2004/0156037 A1* | 8/2004 | Mawhirt | B01L 3/5023 356/39 |

* cited by examiner

*Primary Examiner* — Krishnan S Menon
*Assistant Examiner* — Dwan A Gerido
(74) *Attorney, Agent, or Firm* — Moser Taboada (57) ABSTRACT

The present invention provides a device and a method for blood haemoglobin measurement without carboxyhaemoglobin interference. In the present device and method, oxyhemoglobin, deoxyhemoglobin and methemoglobin are converted into a methemoglobin derivative, i.e. Imidazole-methemoglobin. Imidazole-methemoglobin and carboxyhemoglobin in the matrix are collectively quantified by the reflectance spectroscopy of the matrix at 525 nm, the isobestic point between Imidazole-methemoglobin complex and carboxyhemoglobin molecule.

11 Claims, 4 Drawing Sheets

DEVICE AND METHOD FOR BLOOD HEMOGLOBIN MEASUREMENT WITHOUT CARBOXYHEMOGLOBIN INTERFERENCE

FIELD OF THE INVENTION

The present invention generally relates to a medical device and a method for blood hemoglobin measurement. More specifically, the present invention relates to a biosensor for blood hemoglobin measurement without carboxyhemoglobin interference.

BACKGROUND OF THE INVENTION

Hemoglobin is a metalloprotein of red blood cells and is one of the major constituent of whole blood which is responsible for transporting oxygen in mammals. Hemoglobin primarily exists in five different forms namely, oxy-hemoglobin, deoxy-hemoglobin, methemoglobin, carboxy-hemoglobin and sulfhemoglobin. Only oxy-hemoglobin and deoxy-hemoglobin are involved in oxygen transport; they interconvert into each other in the process of oxygen transportation. Methemoglobin, the oxidized form of hemoglobin in which the iron molecule remains in +3 oxidation state is incapable of transporting oxygen. Carboxy-hemoglobin and sulf-hemoglobin, forms in which iron molecule stays in +2 oxidation state, are also incapable of transporting oxygen since their oxygen binding site stays occupied by strong ligands, CO and S respectively.

Estimation of Hemoglobin is among the most frequent blood tests in pathological practices globally. Total Hemoglobin in whole blood is defined as an algebraic sum of all five forms. Measuring total hemoglobin accurately and in a cost effective manner is a challenging task primarily due to three reasons. First, different forms of hemoglobin have different oxidation states and hence they all cannot be quantified using any single redox reaction. Second, different forms of hemoglobin have different and overlapping optical absorbance spectra with different molar extinction coefficient. Third, due to their high stability, carboxyhemoglobin and sulfhemoglobin do not react readily with most of the reactants, including oxidants and substituents, and hence their optical spectral interference with any hemoglobin derivatives is practically unavoidable. The predominant optical interference in hemoglobin quantification is offered by carboxy-hemoglobin as sulfhemoglobin at maximum is found in traces in whole blood.

The state-of-the-art methods for estimation of total hemoglobin levels can technically be categorized under three categories, discussed as follows: Firstly, the use of pathological blood analyzers, spectrophotometry of unaltered lysed blood at different wavelengths. These analyzers quantify each form of hemoglobin independently by measuring optical absorbance of the blood sample at the peak absorbance wavelengths of each form of hemoglobin. The recorded readings are then interpreted by specialized computing algorithms. Such analyzer systems are highly expensive as they require complex and expensive optical & computing systems.

PCT International Publication No. WO 03/056327 A1 discloses a method for quantitative hemoglobin determination in undiluted unhemolysed whole blood which involves performing a first absorption measurement at a wavelength in the range of 490-520 nm directly on the sample in the cuvette, and further conducting a second absorption measurement, and processing results of first and second absorption measurements to determine the concentration of hemoglobin in the sample.

Spectroscopic method and apparatus for total hemoglobin measurement is disclosed in U.S. Pat. No. 7,449,339B2.

Second method uses non-invasive optical meters, multi-wavelength transmittance method measure transmittance of light of different wavelengths through a part of live body (usually finger tips). Conceptually and operationally similar to electronic non-invasive $SpO_2$ meters, these non-invasive devices measure transmittance at peak absorbance wavelengths of different forms of hemoglobin and measure the percentage of different forms accurately. These percentages values are multiplied with an average hematocrit value to arrive at the absolute concentrations of different forms of hemoglobin. This method is highly error prone as it heavily depends on the assumed hematocrit value, which is different in different samples. As disclosed in U.S. Pat. No. 5,277,181 A entitled "Noninvasive measurement of hematocrit and hemoglobin content by differential optical analysis relates to the noninvasive measurement of blood hematocrit and hemoglobin content using differential optical absorption of two or more wavelengths of light." Also, U.S. Pat. No. 5,692,503 discloses a method for noninvasive (in-vivo) total hemoglobin, oxyhemoglobin, deoxyhemoglobin, carboxyhemoglobin and methemoglobin concentration determination.

Third method is based on hemoglobin chemistry. All forms of hemoglobin are converted either into hemochromogens or hemoglobin derivatives by the action of surfactants or chemicals respectively. The finally developed complex is then quantified optically by measuring its peak absorbance value and correlating that value with concentrations of hemoglobin. It has been experimentally observed that due to very high stability carboxy-hemoglobin remains unaffected by the actions of used reagents. Moreover, carboxy-hemoglobin's optical absorbance spectrum interferes with the spectra of most of the hemoglobin derivatives. With varying concentration of carboxy-hemoglobin, this interference of carboxyhemoglobin leads to inaccuracy in results while quantifying the complex at its peak absorbance wavelength.

Use of reagents in hemoglobin determination have been disclosed in U.S. Pat. Nos. 5,834,315, 3,874,852, 4,800,167, 4,853,338 and US Publication no. US2003/0044995 A1.

As described in U.S. Pat. No. 5,692,503 (A), wavelengths of one or more analytes is selected in the range of 480 nm to 630 nm, with separate analyte wavelength for each hemoglobin species. Thereafter the measurement of individual absorbance of each species is solved for determining the total concentration of hemoglobin.

Devices based on the third method currently follow primarily three approaches described as follows. First approach prefers converting all forms of hemoglobin into hemochromogens by addition of high concentration (above the critical micelle concentration) of detergents and measuring absorbance at the peak absorbance wavelength of hemochromogen. Such approach fails to address the carboxyhemoglobin interference problem. Moreover, since this approach requires measurement of absorbance of blood in reagents coated cuvettes, it requires a large amount of blood sample for testing.

Second approach prefers converting different forms of hemoglobin into a common specie by converting them into a hemoglobin derivative, for example, azide-methemoglobin, and measuring the absorbance or reflectance at the peak absorbance wavelength of the derivative. These methods too fail to convert to the carboxyhemoglobin form to common specie due to highly stability of this form and its resistance to reactivity with most of the chemical reactions.

Use of above-mentioned reagents has been disclosed in STAT-Site MHgb Test System (Stanbio Laboratory Co., Boerne, Tex.), which measures hemoglobin by using a reflectance meter and a hemoglobin test card wherein the test reaction is based on aazidemethemoglobin method. The HemoCue system (HemoCue Inc., Cypress, Calif.) carries a test reaction consisting of sodium deoxycholate, sodium nitrite, and sodium azide nitrite which lyses the blood and converts hemoglobin to hemiglobinazide.

The third approach prefers measuring absorbance or reflectance of lysed blood in its natural state at 523 nm, the natural isobestic point of all four forms of hemoglobin. This method stays under a risk of low sensitivity and poor signal to noise ratio due to three reasons. First, the molar extinction coefficient of different forms of hemoglobin at 523 nm is low (nearly 50% of extinction coefficient of oxy-hemoglobin at its peak absorbance wavelength, 540 nm), resulting in low sensitivity of the device and hence inability to differentiate between different concentrations of hemoglobin. Second, the method is susceptible to low signal to noise ratio as the spectrum of methemoglobin at 523 nm has no clearly differentiated peak and is almost parallel to the abscissa. Third, it has experimentally been found that the absorbance spectra of carboxyhemoglobin and oxyhemoglobin stay close to each other at 523 nm but do not coincide or interest each other at this wavelength. The Hemoglobin test strip and Analysis system disclosed in U.S. Pat. No. 7,379,167 B2 uses an apparatus, which emits light at 522 nm for measurement of hemoglobin concentration. This phenomenon also adds to the inaccuracy of the device.

In light of the above drawbacks in the state-of-the-art there is a need to provide a device and method for blood hemoglobin measurement without carboxyhemoglobin interference thereby providing an accurate result, which addresses the limitations of the state-of-the-art.

SUMMARY OF THE INVENTION

An object of the present invention is to provide a device and a method of hemoglobin measurement without carboxyhemoglobin interference. The present invention relates to a biosensor comprising of disposable strip and electronic reader, for performing blood hemoglobin level estimation.

Another object of the present invention is to provide a novel dry reagent chemistry based system which is portable, simple in usage and does not show false deflections in reading due to change in percentage of carboxyhemoglobin in total hemoglobin in whole blood. Thereby the device and the method for blood hemoglobin measurement in the present invention provide an accurate reading leading to an accurate measurement of blood hemoglobin. Further, this system requires very less amount of blood sample, up to 10 microlitre, making the system easier to use.

In various embodiments of the present invention, the biosensor comprises a strip and an electronic reader for performing blood hemoglobin level estimation.

In accordance with an embodiment of the present invention, the strip is disposable and comprises a polymer layer (1), a matrix (2) resting on a main base (4) impregnated with one or more chemical reagents.

In accordance with an embodiment of the present invention, at least one spacer (3.a, 3.b) is enabled to hold said polymer layer (1), said matrix (2) and said main base (4) in an intact position.

In accordance with an embodiment of the present invention, a photometer comprises a light source (8) wherein said disposable strip is placed in a detection area comprising a sample of said blood hemoglobin aligned at one end of said light source (8) allowing reflected rays through an optical slit (5).

In accordance with an embodiment of the present invention, a processing unit controls said light source (8) of a particular wavelength, 525 nm which—as per the invention—has been found to be the isobestic point of imidazole-methemoglobin complex and carboxyhemoglobin molecule, by flashing the said light source (8).

In accordance with an embodiment of the present invention, a processing unit comprises a microcontroller or a microprocessor.

In accordance with an embodiment of the present invention, one or more photo-sensors (6.a, 6.b) placed at one end of said one or more optical barriers angled to allow reflectance photometry on at least one surface of one or more photo-sensors (6.a, 6.b). In accordance with an embodiment of the present invention, an optical filter placed between said light source (8) and said strip.

In accordance with an embodiment of the present invention, a control unit reads a signal from a potential generated across one or more photo-sensors due to falling of one or more reflected rays upon one or more photo-sensors (6.a, 6.b).

In accordance with an embodiment of the present invention, an analog to digital converter converts said signal to a digital value and a digital correlation that correlates said value to an output interface including a display screen.

In accordance with an embodiment of the present invention, the chemical reagents are selected from a group of one or more lysing agents comprising diocetyl sodium sulfosuccinate, sodium dodecyl benzene sulphonate, lauryl dimethylamine oxide, octylphenoxypolyethoxy ethanol, potassium ferricyanide, sodium lauryl sulfate, lithium dodecyl sulfate, sodium nitrite, sodium myristyl sulfate, cetyl trimethyl ammonium bromide, sodium dodecylsulfate, sodium deoxycholate, N-lauroylsarcosine, triton-X 100, hydrochloric acid, sodium nitrite or their mixtures present in range of 0.1% to about 10% (w/v) and a ligand consisting of imidazole.

In accordance with an embodiment of the present invention, the reagents generate a methemoglobin molecule and the ligand, Imidazole is coupled to the methemoglobin molecule to form said imidazole-methemoglobin complex.

In accordance with an embodiment of the present invention, the polymer layer (1) is made of a material comprising a nylon treated with one of more said reagents, said matrix (2) is made of a micro-porous, uniformly thick, hydrophilic, polymeric material and said main base is made up of a hard, opaque and hydrophobic polymer, including polyurethane, polyvinylchloride, polycarbonate or styrene (4).

In accordance with an embodiment of the present invention, the light source (8) emits 525 nm periodically for a period of 200 millisecond, frequenting at one or more flashes per second.

In accordance with an embodiment of the present invention, at least one optical barrier (7.a, 7.b) is placed at an angle of 60° with respect to another optical barrier forming an equilateral triangle and with said light source (8) placed at an incentre of said equilateral triangle.

In accordance with an embodiment of the present invention, the control unit is a microcontroller based electronic unit to read an analog signal obtained from an analog potential generated across one or more photo-sensors due to falling of said reflected light upon one or more photo-sensors (6.a, 6.b).

In accordance with an embodiment of the present invention, the analog to digital converter converts analog signal into a digital value and said microcontroller or microprocessor records said digital values across said one or more photo-sensors (6.a, 6.b) of 525 nm once at every ten millisecond in 100 milliseconds.

In accordance with another embodiment of the present invention, an operational amplifier amplifies said digital values, a signal analysis unit interprets said amplified digital values and compares said amplified digital values by said values stored in said microcontroller and displays a corresponding output value on said display screen.

Yet another embodiment of the present invention is to provide said method for blood hemoglobin measurement which comprises the steps of: establishing an isobestic point of 525 nm between an imidazole-methemoglobin complex and a carboxyhemoglobin molecule, preparing one or more layers (1,2,4) of a disposable strip placed in a detection area impreganted with at least one chemical reagent, converting a oxyhemoglobin, a deoxyhemoglobin and a methhemoglobin molecule into a common molecule, placing at least one photosensor (6.a, 6.b) at one end of at least one optical barrier to allow reflection to reach at least one surface of one or more photosensors (6.a, 6.b), reading of an analog potential in said analog signal form generated across at least one photo-sensor (6.a, 6.b) due to falling reflected light rays upon at least one photo-sensor (6.a, 6.b) and displaying a corresponding output value on a display screen.

In accordance with another embodiment of the present invention, the oxyhemoglobin molecule, deoxyhemoglobin molecule converted into a methemoglobin molecule by one or more of said reagents.

In accordance with another embodiment of the present invention, the ligand consisting of imidazole is coupled with methemoglobin to form said imidazole-methemoglobin complex.

In accordance with another embodiment of the present invention, performing reflectance photometery at a single wavelength of said isobestic point of 525 nm involves placing said strip at one end of said light source (8) comprising a light source corresponding to generation of light of 525 nm as wavelength and allowing a plurality of reflected rays through said optical slit (5) to said strip and aligning one or more optical barriers (7.a, 7.b) at an angle of 60° to one or more optical barriers (7.a, 7.b).

In accordance with another embodiment of the present invention, controlling said light source (8) by a microcontroller or a microprocessor and flashing said light source periodically for said period of 200 millisecond, frequenting at one or more flashes per second.

In accordance with another embodiment of the present invention, an analog potential in said analog signal form is read by a microcontroller or microprocessor based electronic system.

In accordance with another embodiment of the present invention, the analog signal is converted into at least one digital value through a analog to digital converter.

In accordance with another embodiment of the present invention, recording and averaging said digital values across said one or more photo-sensors (6.a, 6.b) is done once at every ten millisecond in 100 milliseconds.

In accordance with another embodiment of the present invention, ten said consecutive tenth millisecond readings are averaged to generate a 100 milliseconds average value.

In accordance with another embodiment of the present invention, the 100 millisecond average value of the 100 millisecond period preceding the period when the light source is turned on is stored as a $V_{off}$ value and two consecutive batches of 100 millisecond average values are recorded during the period when the light source is turned on.

In accordance with another embodiment of the present invention, a second average value is recorded as a $V_{on}$.

In accordance with another embodiment of the present invention, a difference between $V_{on}$ and $V_{off}$, noted as a Delta V value and consecutive values of Delta V are recorded until the values of consecutive Delta V become similar or close to similar.

In accordance with another embodiment of the present invention, the last recorded Delta V value is compared with at least one digital value stored in said microcontroller or microprocessor and said corresponding output value is displayed on said display screen.

BRIEF DESCRIPTION OF DRAWINGS

For a better understanding of the aforementioned embodiments of the invention as well as additional embodiments thereof, reference should be made to the Description of Embodiments below, in conjunction with the exemplary figures wherein.

DETAILED DESCRIPTION OF THE INVENTION

In the following detailed description, numerous specific details are set forth in order to provide a thorough understanding of some embodiments of the invention. However, it will be understood by persons skilled in the art that the embodiments may be practiced without any specific details. In other instances, well-known methods, procedures, components and/or systems have not been described in detail so as not to obscure the discussion.

It will be appreciated that the embodiments of the invention hereinbefore described are given by way of example only, and are not meant to limit the scope of the invention in any way.

The present invention provides a device and a method for blood hemoglobin measurement without carboxyhemoglobin interference. The present invention is a biosensor for performing for accurate, rapid and convenient blood hemoglobin level estimation. The present system comprises the following components:

A strip:

In the present invention, the strip is disposable and has a unique biochemistry to lyse red blood cells of whole blood and to convert oxyhemoglobin, deoxyhemoglobin and methemoglobin into a common molecule using at least one chemical reagent impregnated in a disposable strip, and then to quantify optical absorbance of the sample by reflectance spectroscopy at the isobestic point of the common molecule and carboxyhemoglobin. The common molecule formed should have high extinction coefficient at the isobestic point and high optical resolution at the isobestic point, with respect to other wavelength.

At least one chemical reagent embedded in said disposable strip can be selected from a group of at least one reagent comprising diocetyl sodium sulfosuccinate, sodium dodecyl benzene sulphonate, lauryl dimethylamine oxide, octylphenoxypolyethoxy ethanol, potassium ferricyanide, sodium lauryl sulfate, lithium dodecyl sulfate, sodium nitrite, sodium myristyl sulfate, cetyl tri-methyl ammonium bromide, sodium dodecylsulfate, sodium deoxycholate, N-lauroylsarcosine, triton-X 100, hydrochloric acid, sodium nitrite or their mixtures present in range of 0.1% to about 10% (w/v) and a ligand consisting of imidazole.

The present device extracts different forms of hemoglobin from red blood cells (RBC) and converts oxyhemoglobin, deoxyhemoglobin and methemoglobin into a single molecule in the following steps: First, the red blood cells in blood hemoglobin are lysed, second, the oxyhemoglobin and deoxyhemoglobin molecules are converted to methemoglobin, and third, methemoglobin is converted into imidazole-methemoglobin. These steps are performed by the action of said at least one chemical reagent impregnated in the disposable strip (FIG. 1) in dry state. When blood passes through the strip chemical reactions take place in sequence and in parallel.

Among the three molecules of interest (oxyhemoglobin, deoxyhemoglobin and methemoglobin) in blood, since methemoglobin is the oxidized form of hemoglobin and is chemically difficult to reduce, hence rest of the two molecules (oxyhemoglobin and deoxyhemoglobin) are converted into methemoglobin using said at least one chemical reagent. Further, to increase the optical sensitivity and signal to noise ratio of the system the resulting methemoglobin is converted into a methemoglobin derivative by binding it with a ligand consisting of imidazole.

Since carboxyhemoglobin is a highly stable compound and does not react with any chemical used in the strip, carboxyhemoglobin stays unaffected by any chemical. Hence, after passing through the polymer and the matrix layers the blood sample consists of only two derivatives of hemoglobin—the methemoglobin derivative and carboxyhemoglobin.

The methemoglobin derivative that forms in the strip of the present invention is imidazole-methemoglobin. In the present invention, the isobestic point between imidazole-methemoglobin and carboxyhemoglobin is 525 nm. As the molar extinction coefficient of carboxyhemoglobin and Imidazole-methemoglobin at 525 nm is quite high than the molar extinction coefficient of any of the four hemoglobin derivatives (oxyhemoglobin, deoxyhemoglobin, methemoglobin and carboxyhemoglobin) at 523 nm which is the natural isobestic point of oxyhemoglobin, deoxyhemoglobin, methemoglobin and carboxyhemoglobin and hence sensitivity of the system is very high. Moreover, as established, due to spectral characteristics of imidazole-methemoglobin the signal to noise ratio of the complex is also high than that of other natural species.

Architecture of said disposable strip:

When blood is dropped on the strip, if first encounters the first layer—a polymer layer (1), which is made of a material comprising a nylon treated with said at least one chemical reagent. After passing through the polymer layer the blood travels through the second layer—a matrix (2) which is made of a micro-porous, uniformly thick, hydrophilic, polymeric material comprising said at least one chemical reagent. The matrix rests over the third layer, a main base (4) composed of a hard, opaque and hydrophobic polymer, including polyurethane, polycarbonate, styrene, polyvinylchloride sheet (4) which gives the strip its shape and stability.

In the present invention, the disposable strip's architecture has the following advantages: (a) it performs different biochemistry steps described above; (b) mass manufacturing process of these strips are simple so that the manufacturing is standardized and affordable; and (c) the strip design is user friendly.

Figure 1:
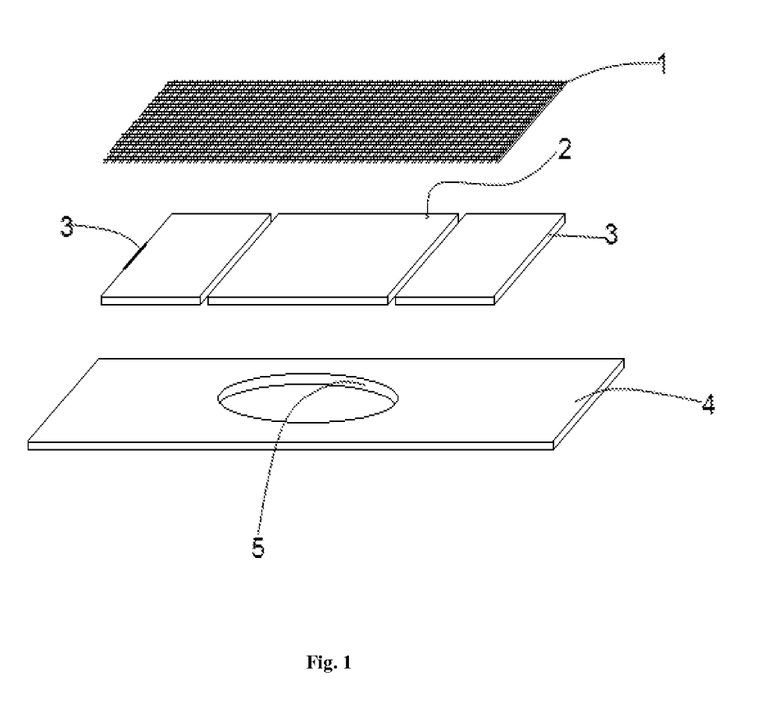
FIG. 1 illustrates a perspective front view of different layers of the disposable strip.

FIG. 1 illustrates a layer by layer representation of the disposable strip. The strip is impregnated with said at least one chemical reagent wherein said at least one chemical reagent adsorbed in the polymer layer (1) lyses the RBCs and converts oxyhemoglobin and deoxyhemoglobin to methemoglobin. The polymer's material—nylon is treated with a non-ionic detergent to impart a balanced level of hydrophilicity, only enough to facilitate contact with the blood sample for uniform and rapid dispersion across it while keeping sample absorption & retention minimal.

Impregnated with said at least one chemical reagent, the micro-porous polymeric matrix (2) is used for forming the ligand derivative. The side of the matrix that faces incident light must have smooth surface finish to minimize noise in signals. The matrix must have high hydrophilicity so that it may disperse the sample evenly and rapidly. The thickness of the matrix must be optimized such that it gives enough path-length to the sample for completion of reaction with the impregnated ligand. However, the pore size, dimensions and thickness of the matrix must be optimized such that it requires minimum amount of blood sample for a test. The rate of dispersion of blood sample across the matrix can be optimized by impregnating a low concentrations of surfactant.

Figure 3:
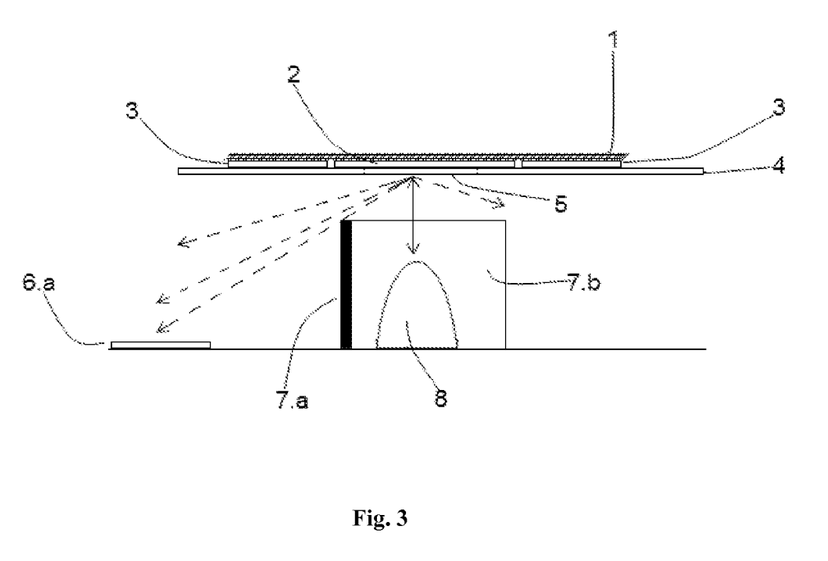
FIG. 3 illustrates a perspective front view explaining the ray optics of reflectance photometry.

Spacers (3.a & 3.b) are placed to hold the polymer layer (1), said matrix (2) and the base (4) together and to provide the polymer layer a flat surface above the matrix so that the blood sample disperses across the polymer uniformly. They must be of similar thickness as of matrix and should have non-reacting adhesive coatings on both sides. The said base (4) should be hard enough to be maneuvered by any user, while being thinnest possible to minimize optical path length and maximize reflected rays. As illustrated in FIG. 3, the dimensions of the optical slit (5) should be kept to optimize the sensitivity of the electronic transducing system's sensitivity while minimizing the matrix's requirement and hence the blood sample requirement for testing.

A Photometer:

The photometer has been designed to perform reflectance photometry at a single wavelength (FIG. 3). The wavelength used in our system is the isobestic point between the methemoglobin derivative and carboxyhemoglobin. The above isobestic point of 525 nm was established between said ligand and said at least one chemical reagent involved in converting oxyhemoglobin and deoxyhemoglobin to methemoglobin. Thereafter the isobestic point between imidazole-methemoglobin and carboxyhemoglobin of 525 nm was concluded. The sample (strip here) is placed on a region called as detection area which stays directly above the light source so that the light falls perfectly on the sample strip.

Figure 2:
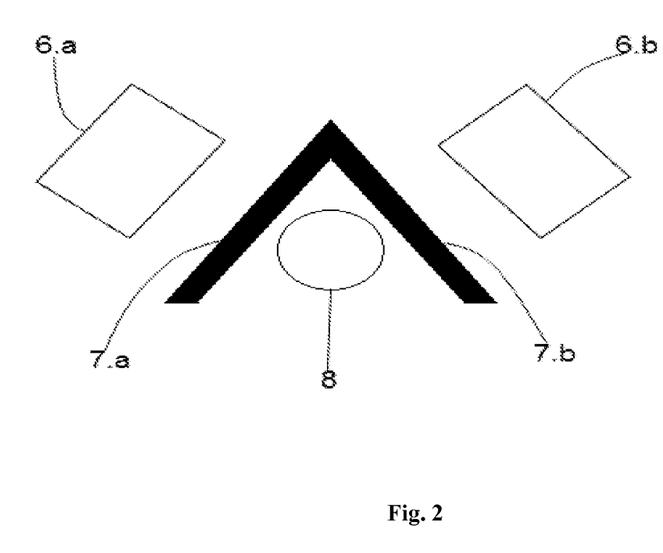
FIG. 2 illustrates top view of the optical reflectance transducer.
Figure 4:
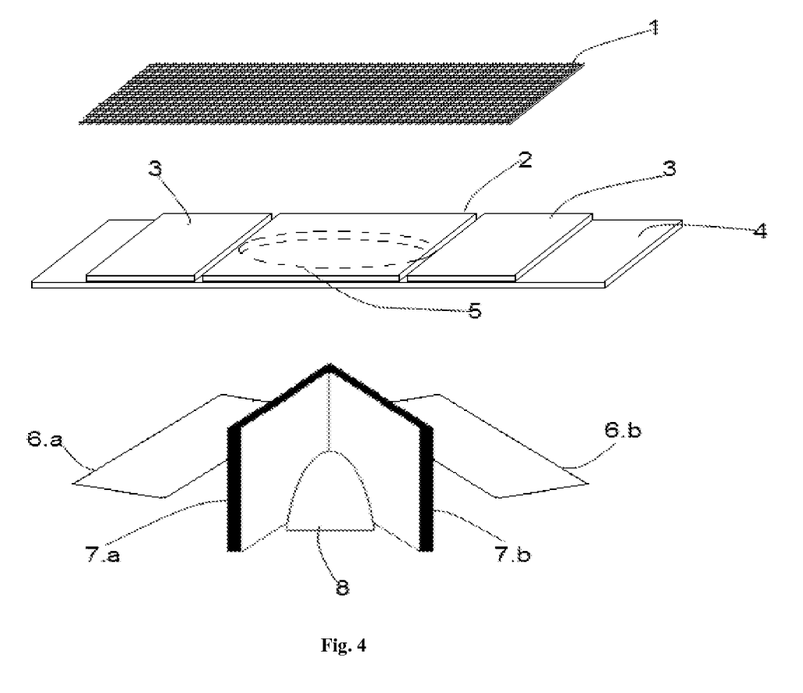
FIG. 4 illustrates a perspective front view representing dimensions and positions of different component with respect to each other.

FIG. 2 shows the top view of the optical design of the reader. The reader is designed in such a manner that the sensitivity of the system is amplified and uniformity of dispersion of blood across the matrix is automatically verified. The light source (8) of 525 nm may be surrounded by one or two optical barriers (7.a & 7.b). The equally sized optical barriers may be placed at an angle of 60° to each other such that they stand on the sides of a hypothetical equilateral triangle (as shown in FIG. 4). Optical barriers prevent a transmittance of direct light from the light source to the photo-sensors (6.a & 6.b). Position of the light source (8) is fixed at the incenter of the equilateral triangle. One or two photo-sensors (6.a & 6.b) of 525 nm may be symmetrically placed behind the optical barriers at such a distance from the barrier that only a component of reflection may reach on their surface. To decrease the noise in the optical signal an optical filter may be used between the path of the light source and the sample (strip) so that near to monochromatic light (of wavelength 525 nm) falls on the strip. Using two photo-sensors (6.a & 6.b) may help in increasing the system's sensitivity as two photo-sensors can collect more of said component of reflected light (as shown in FIG. 3).

Signal analysis and error correction method:

The potential generated across the photo-sensors by falling light on its light sensitive area is recorded by a unique method by the present device. Since our system's detection principle is optical, any external light is bound to interfere with the readings. To avoid effects of ambient light of the system a unique approach is followed. The light source is controlled by a processing unit comprising a microcontroller or a microprocessor of the electronic of the system, which is flashed periodically for a period of 200 millisecond (ms), frequenting at 1-2 flashes per second. The digital values generated across the photo-sensors (6.a & 6.b) are continuously recorded periodically once at every 10 millisecond. Ten adjacent recorded values (in 100 milliseconds) is averaged and stored. This averaging of reading is done to minimize electronic noise. Moreover, appropriate logical filters are applied to screen off fluctuations in readings occurred due to presence of any external magnetic field or any other electronic signal interferent. The flashing of light source and recording data across the photo-sensor is started at the same coordinate on the time scale. Flashing light source and storing observed potential readings across photosensors (6.a & 6.b) at different frequencies enable us to have two different set of recorded data—first, corresponding to those during which the light source (8) was flashing ($V_{on}$) and second, corresponding to those during which the light source was not flashing ($V_{off}$).

In the flashing period of 200 ms, we receive two readings of $V_{on}$, i.e, $Von^1$ and $Von^2$, out of which one of the readings is selected as Von for further analysis. The reading corresponding to only said component of reflected light should be deduced as the difference between the values of Von and $V_{off}$. Careful experimental evaluations also show constructive optical interference of said component of reflected light and ambient light. This interference leads to addition of another factor in Von with increasing ambient light. Therefore, a correction factor corresponding to empirically deduced effect of changing ambient light may also be amended to the system. The net result is proportional to the signal. Said signals taken repeatedly along with time when stabilize generate a final value, which may have linear, polynomial, exponential or logarithmic correlation with the concentration of hemoglobin in the blood samples.

A control unit comprising a microcontroller or a microprocessor based electronic system reads the analog potential generated across the photo-sensor due to falling of said component of reflected light upon it. The analog signal is then converted into digital values through an analog to digital converter. The digital values are amplified by using operational amplifier. The amplified digital values are then interpreted as per the signal analysis methodology of the system. The interpreted value is then compared by values stored in the microcontroller. A corresponding output may be then generated on a display.

Functions, operations, components and/or features described herein with reference to one or more embodiments, may be combined with, or may be utilized in combination with, one or more functions, operations, components and/or features described herein with reference to one or more other embodiments, or vice versa.

While certain features of some embodiments of the invention have been illustrated and described herein, many modifications, substitutions, changes, and equivalents may occur to those skilled in the art. It is therefore, to be understood that the appended claims are intended to cover all such modifications and changes.

I claim:

1. A device for measuring total blood hemoglobin comprising:
   a strip comprising at least one layer impregnated with chemical reagent comprising imidazole and effective to (i) lyse red blood cells to release oxyhemoglobin, deoxyhemoglobin, and methemoglobin molecules, (ii) convert the oxyhemoglobin and deoxyhemoglobin to methemoglobin, and (iii) convert the methemoglobin into imidazole-methemoglobin;
   a support enabled to hold said at least one layer in an intact position;
   a photometer comprising a light source wherein said strip is placed in a detection area comprising a sample of said blood hemoglobin aligned at one end of said light source allowing reflected rays through an optical slit;
   a processing unit that controls said light source of a wavelength of 525 nm, the isobestic point of imidazole-methemoglobin complex and carboxyhemoglobin molecule, by flashing said light source;
   at least one photo-sensor placed at one end of at least one optical barrier placed to allow reflected light on a surface of at least one photo-sensor;
   an optical filter placed between said light source and said strip;
   a control unit that reads a signal from a potential generated across at least one photo-sensor due to falling of at least one reflected ray upon at least one photo-sensor;
   an analog to digital converter that converts said signal to a digital value; and
   an output interface displaying on a display screen a total blood hemoglobin value that is based on said digital value,
   wherein the device is configured to read the absorption at 525 nm of hemoglobin molecules derived from said blood sample in order to obtain the digital value.

2. The device for blood hemoglobin measurement as claimed in claim 1, wherein said light source flashes light of said 525 nm periodically for a period of 200 millisecond, frequenting at least one flash per second.

3. The device for blood hemoglobin measurement as claimed in claim 1, wherein said at least one optical barrier placed at an angle of 60° with respect to another optical barrier forming two sides of a hypothetical equilateral triangle with said light source placed at an incentre of said equilateral triangle.

4. The device for blood hemoglobin measurement as claimed in claim 1, wherein said at least one layer comprises a polymer layer, a matrix resting on a main base.

5. The device for blood hemoglobin measurement as claimed in claim 4, wherein said polymer layer is made of a material comprising a nylon treated with said at least one reagent, said matrix is made of a micro-porous, uniformly thick, hydrophilic, polymeric material and said main base is made of a hard, opaque and hydrophobic polymer, including polyurethane, polyvinylchloride, polycarbonate, styrene.

6. The device for blood hemoglobin measurement as claimed in claim 1, wherein said chemical reagents comprise a surfactant selected from a group of at least one reagent comprising, sodium dodecyl benzene sulphonate, lauryl dimethylamine oxide, octylphenoxypolyethoxy ethanol, sodium lauryl sulfate, lithium dodecyl sulfate, sodium myristyl sulfate, cetyl tri-methyl ammonium bromide, sodium dodecylsulfate, sodium deoxycholate, N-lauroylsarcosine, triton-X 100 or their mixtures present in a range of 0.1% to about 10% (w/v).

7. The device for blood hemoglobin measurement as claimed in claim 6, wherein said chemical reagents comprise potassium ferricyanide and sodium nitrite.

8. The device for blood hemoglobin measurement as claimed in claim 1, wherein said control unit is a microcontroller or microprocessor based electronic unit to read an analog signal obtained from an analog potential generated across said at least one photo-sensor due to falling of said reflected light upon said at least one photo-sensor.

9. The device for blood hemoglobin measurement as claimed in claim 8, wherein said analog to digital converter converts said analog signal into a digital value and said processing unit records said digital values across said at least one photo-sensor once at the end of every tenth millisecond.

10. The device for blood hemoglobin measurement as claimed in claim 9, wherein an operational amplifier amplifies said digital values, a signal analysis unit interprets said amplified digital values and compares an amplified digital values by said values stored in said processing unit and displays a corresponding output value on said display screen.

11. A device for measuring total blood hemoglobin comprising:
a strip comprising at least one layer impregnated with chemical reagents comprising imidazole and effective to (i) lyse red blood cells to release oxyhemoglobin, deoxyhemoglobin, and methemoglobin molecules, (ii) convert the oxyhemoglobin and deoxyhemoglobin to methemoglobin, and (iii) convert the methemoglobin into imidazole-methemoglobin, and configured to provide the imidazole-methemoglobin and carboxyhemoglobin for optical measurement;
a photo detection unit configured to measure light absorption signal at a wavelength of 525 nm, the isobestic point of imidazole-methemoglobin complex and carboxyhemoglobin molecule, of the provided the imidazole-methemoglobin and carboxyhemoglobin; and
an output device configured to output a total blood hemoglobin value that is based on a digital value derived from the signal for the absorption at 525 nm.

* * * * *